United States Patent [19]
Machek et al.

[11] Patent Number: 4,938,230
[45] Date of Patent: * Jul. 3, 1990

[54] DEVICE FOR SELECTIVELY PRODUCING INCREMENTAL JOINT MOVEMENT IN A PATIENT IN OPPOSITE DIRECTIONS

[75] Inventors: James E. Machek, Bradfordwoods; Edward J. Rhinehart, Monroeville, both of Pa.

[73] Assignee: Medrad, Inc., Pittsburgh, Pa.

[*] Notice: The portion of the term of this patent subsequent to May 30, 2006 has been disclaimed.

[21] Appl. No.: 331,811

[22] Filed: Mar. 31, 1989

Related U.S. Application Data

[63] Continuation-in-part of Ser. No. 19,459, Feb. 26, 1987, Pat. No. 4,834,112.

[51] Int. Cl.⁵ .............................................. A61B 5/10
[52] U.S. Cl. ..................................... 128/777; 128/20; 33/514
[58] Field of Search ................. 128/20, 774, 777, 782, 128/341–345; 33/143 R, 143 C, 143 J, 143 K, 143 M, 144, 511–515

[56] References Cited

U.S. PATENT DOCUMENTS

| | | | |
|---|---|---|---|
| 1,217,745 | 2/1917 | Gracey | 128/20 |
| 1,706,500 | 3/1920 | Smith | 128/20 |
| 1,823,045 | 9/1931 | Hommel | 33/143 J |
| 2,245,959 | 6/1941 | Brown | 33/143 J |
| 2,450,194 | 9/1948 | Glaser | 128/20 |
| 3,752,149 | 8/1973 | Ungar et al. | 128/20 X |
| 4,151,837 | 5/1979 | Millard, Jr. et al. | 128/20 X |
| 4,263,899 | 4/1981 | Burgin | 128/20 X |
| 4,337,762 | 7/1982 | Gauthier | 128/20 |
| 4,344,420 | 8/1982 | Forder | 128/20 |
| 4,469,108 | 9/1984 | Goldstein | 128/774 X |
| 4,606,128 | 9/1986 | Wyrwich et al. | 33/143 C |
| 4,627,421 | 12/1986 | Symbas et al. | 128/20 |

FOREIGN PATENT DOCUMENTS 1082417  3/1984  U.S.S.R. .............. 128/341

*Primary Examiner*—Angela D. Sykes
*Attorney, Agent, or Firm*—Fleit, Jacobson, Cohn, Price, Holman & Stern

[57] ABSTRACT

A device for selectively providing precise incremental joint movement in a patient in either of two opposite directions with a tactile and audible feedback "click", includes first and second spaced disposable retractors for engaging respective parts of the patient adjacent the joint. One of the retractors is mounted on a fixed, inverted, U-shaped support member, and the other retractor is mounted on a movable actuating rod slidably mounted in the support member. The device is formed entirely of non-magnetic material and is readily operable by the patient, making the device especially useful in magnetic resonance imaging procedures. An operating mechanism for the actuating rod includes a pivoted operating handle having an integral drive pawl, and a retaining mechanism for the actuating rod includes a pair of resilient retaining or holding pawls pivoted on the support member adjacent opposite sides of the drive pawl. The operating handle is pivoted on a rockable lifting lever of a retractor quick-release mechanism, so that rocking of the lifting lever raises the handle which, in turn, raises and pivots the holding pawls to release the actuating rod so that it can be readily moved by hand in either of the opposite directions.

30 Claims, 3 Drawing Sheets

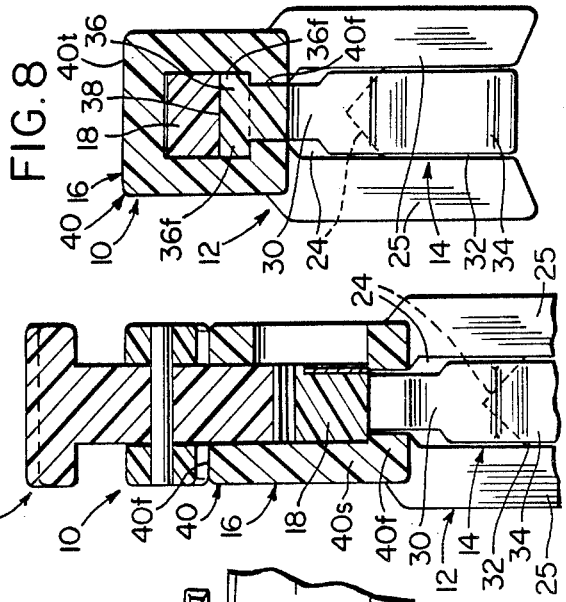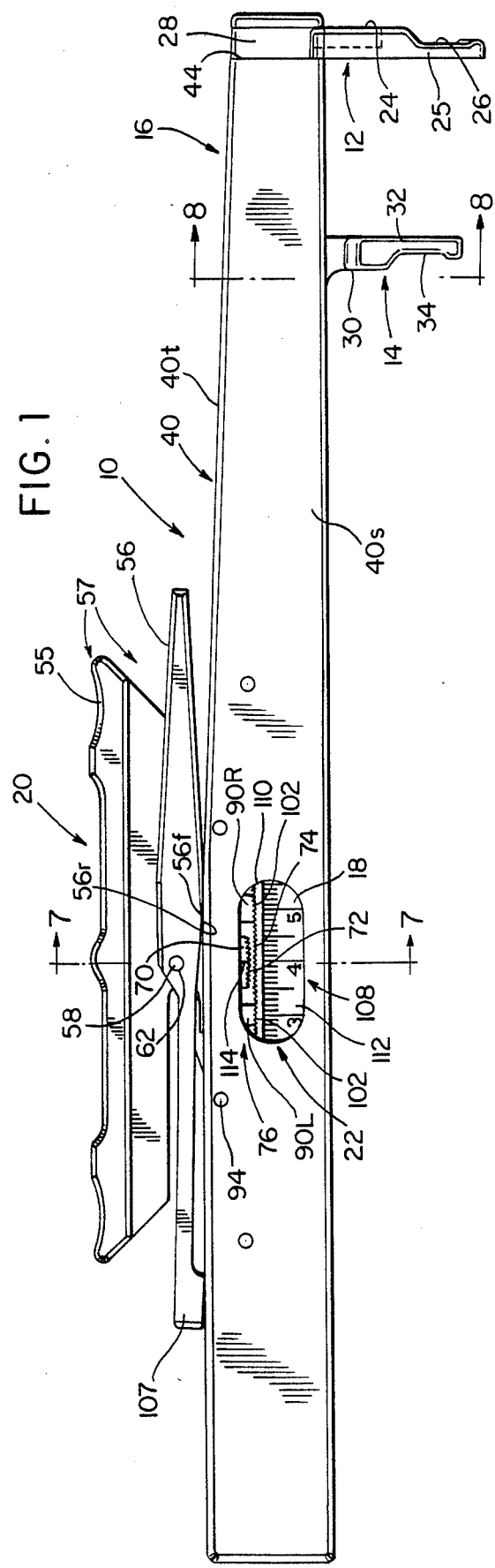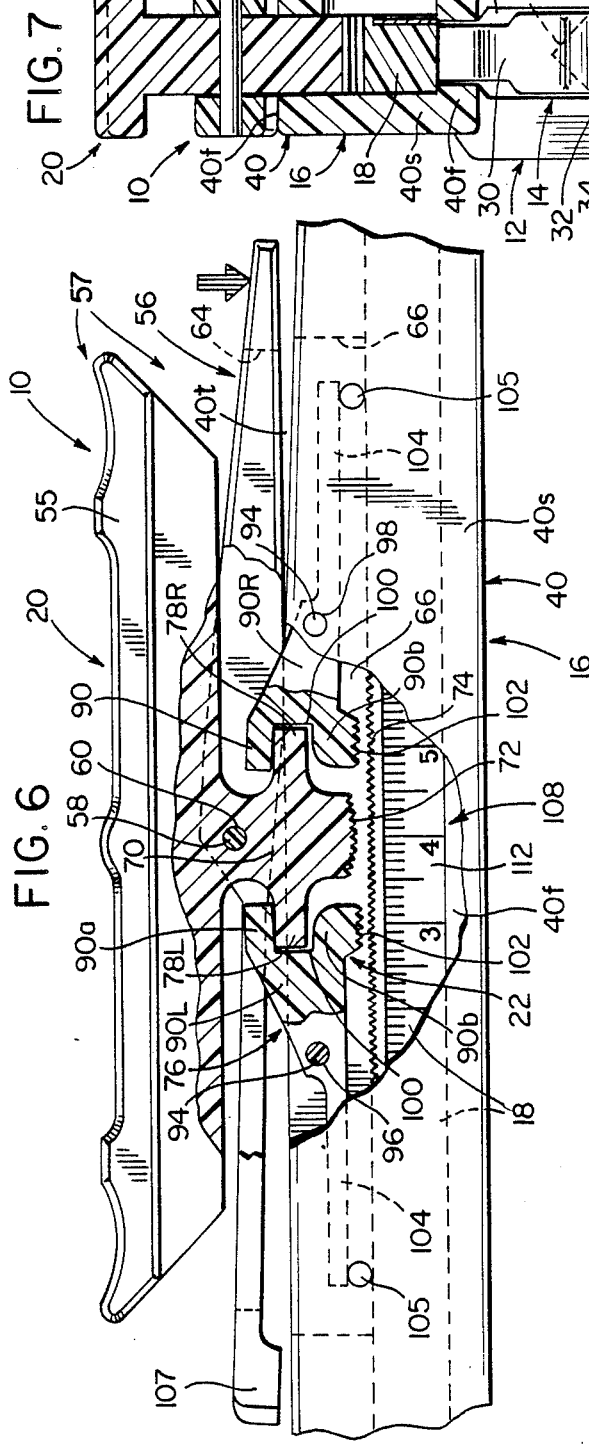

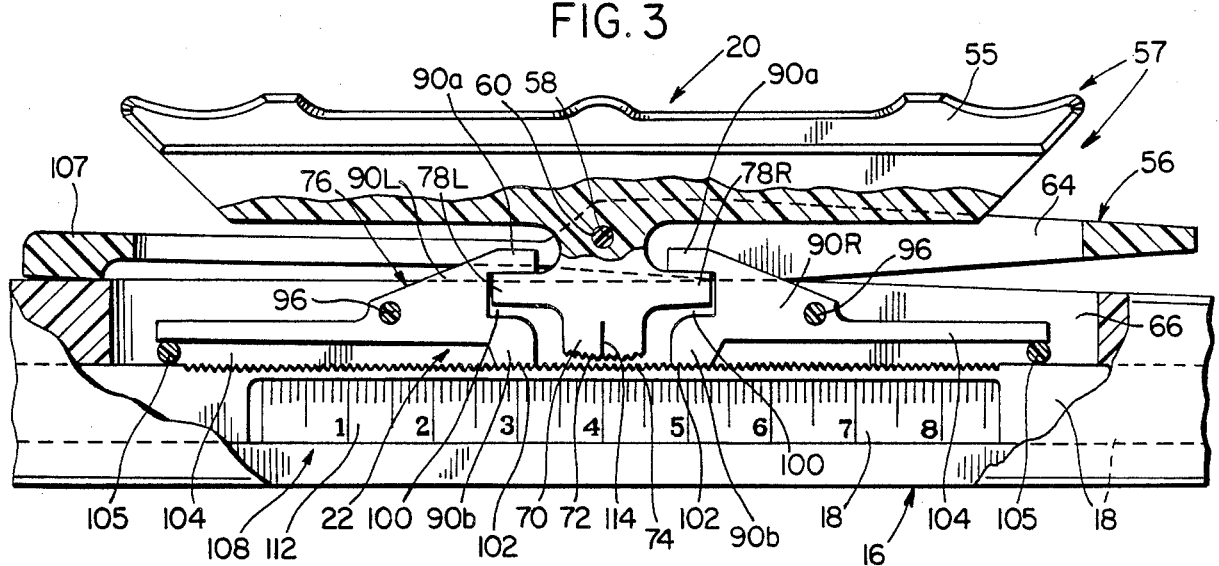
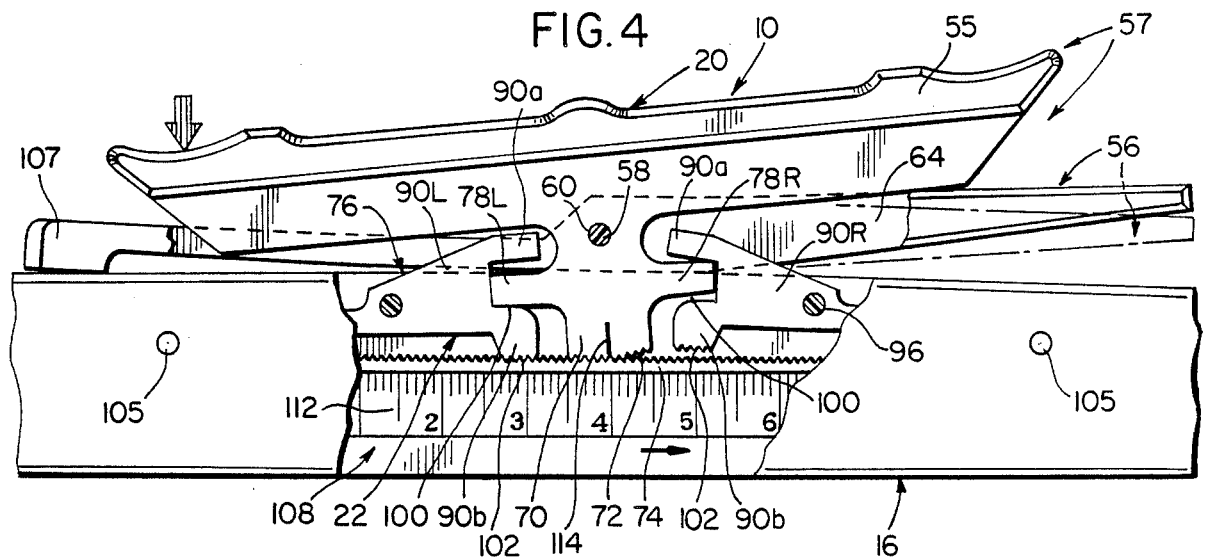
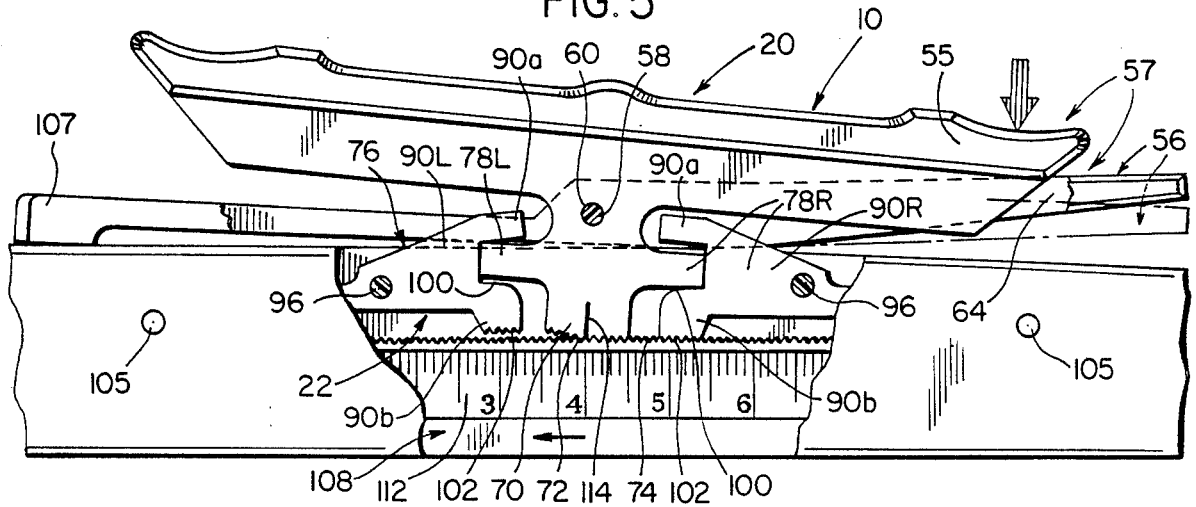

DEVICE FOR SELECTIVELY PRODUCING INCREMENTAL JOINT MOVEMENT IN A PATIENT IN OPPOSITE DIRECTIONS

This is a continuation-in-part of application Ser. No. 07/019,459, filed Feb. 26, 1987, now U.S. Pat. No. 4,834,112.

BACKGROUND OF THE INVENTION

1. Field of the Invention

The present invention relates generally to a device for producing precise incremental joint movement in a patient, and more specifically to a device for selectively producing precise temporalmandibular joint movement in a patient in either of two opposite directions, wherein the device is operated by the patient during the making of internal images of the joint by magnetic resonance imaging.

2. Description of Related Art

It is known to diagnose various disorders, such as joint pain, by viewing internal images of the area under investigation at stepped positions. Such investigations can be performed by standard x-rays, by the new CT scan or by the even newer technique of magnetic resonance imaging (MRI).

For example, patients may suffer from a temporalmandibular joint (TMJ) disorder in which opening or closing of the lower jaw can be accomplished, if at all, only with severe pain or discomfort. Treating of these patients involves personal observation by a physician, the accuracy of which can be significantly enhanced with the aid of a series of internal images made of the jaw area at spaced stages of jaw opening through MRI techniques.

In the past, the progressive opening of the temporalmandibular joint for the above diagnosis has been accomplished by the physician or a technician inserting a wedge-type dental block between the patient's jaw bones (i.e., teeth) and forcing the block rearward in "slow" incremental steps. A scissors-like forceps, having a releasable pawl mechanism for locking the forceps in each stage of jaw opening, also has been used.

However, the foregoing procedures have a number of disadvantages. For example, the use of the manually inserted, wedge-type dental block is relatively inaccurate and requires the presence of a physician or technician with the patient during the insertion procedure. The scissors-like forceps, while more accurate, is cumbersome and unwieldy, and still requires great care in order to achieve evenly spaced steps. Prior art devices also usually comprise at least some magnetic material and, therefore, are not suitable for magnetic resonance imaging.

To overcome the shortcomings of the prior art, U.S. patent application Ser. No. 07/019,459, filed Feb. 26, 1987, now U.S. Pat. No. 4,834,112, of which this application is a continuation-in-part and which is assigned to the same Assignee as this application, discloses a precise device for producing incremental joint movement in a patient, which contains no materials with magnetic properties and which, therefore, is suited for use in magnetic resonance imaging. This device accomplishes temporalmandibular joint incrementing in a magnetic resonance imaging procedure precisely and simply, and may be patient-operated so as to not require the immediate presence of a physician or technician with the patient. However, this device is capable of incrementing in only one direction, whereas in certain instances it is desirable to have the capability of both opening and closing a joint in precise increments (e.g., selectively reversing directions) during the same diagnostic procedure.

Accordingly, a non-magnetic device is needed by which temporalmandibular joint incrementing in a magnetic resonance imaging procedure can be achieved precisely and simply in either of two opposite directions, without the immediate presence of a physician or technician with the patient, and the primary purpose of the present invention is to provide such a device.

SUMMARY OF THE INVENTION

In general, the present invention relates to a device for selectively and precisely incrementing joint movement in a patient in either of two opposite directions, the device comprising first and second spaced retractors, which preferably are disposable, for engaging respective body parts of the patient adjacent the joint. The device further includes a support having the first and second retractors mounted on the support for relative movement and an actuating mechanism mounted on the support to cause relative movement between the first and second retractors. An operating mechanism is provided on the support for producing a precise preselected incremental movement of the actuating mechanism. By a single stroke of the operating mechanism, the second retractor moves into a precise incremented position relative to the first retractor, selectively in either of the two opposite directions. A mechanism also is provided on the support for retaining the actuating mechanism and the first and second retractors in their relative incremented positions.

More specifically, the support comprises a holder portion by which the device is adapted to be held by one hand of a user operating the device. The support is of elongated, U-shaped construction, and the actuating mechanism is an elongated rod slidably mounted in the elongated, U-shaped support. The operating mechanism includes a pivoted operating handle having an integral drive pawl member engageable with teeth on the actuating rod, and the retaining mechanism comprises a pair of spring-biased pivoted retaining or holding pawl members, also engageable with the teeth on the actuating rod. The operating handle can pivot in opposite directions to cause the integral drive pawl to precisely increment the actuating rod and the second retractor in the desired direction with each stroke of the operating handle. Pivoting of the operating handle also causes lifting of one of the retaining pawls out of engagement with the teeth on the elongated actuating rod. At the same time, the other retaining pawl rides out of the associated teeth on the elongated rod, and then is reseated by a lug on the operating handle into the next adjacent teeth on the actuating rod with a tactile and audible feedback "click". The operating handle, which also forms part of a retractor quick-release mechanism, is pivoted on a retaining pawl lift lever which, when pivoted, lifts the operating handle to elevate both retaining pawls simultaneously so that the actuating rod can be moved manually in either direction. The first retractor, which is mounted upon the U-shaped support, includes a pair of spaced projecting patient-engaging legs, and the second retractor, which is mounted upon the elongated actuating rod, includes a single patient-engaging leg receivable in a space between the patient-engaging legs of the first retractor when the device is in the start position.

BRIEF DESCRIPTION OF THE DRAWINGS

FIG. 1 is a schematic side view of a patient joint incrementing device in accordance with the invention, in a locked, non-incrementing neutral condition;

FIG. 3 is an enlarged side view of part of the device shown in FIG. 1, partially broken away and in cross-section, illustrating the interior of the device in the locked, non-incrementing neutral condition;

FIG. 4 is a side view similar to FIG. 3, showing the device in a first incrementing condition in one direction;

FIG. 5 is a side view similar to FIG. 3, showing the device in a second incrementing condition in an opposite direction;

FIG. 6 is a side view similar to FIG. 3, showing the device in an unlocked released condition;

FIG. 7 is an enlarged cross-sectional view taken along the line 7—7 in FIG. 1; and FIG. 8 is an enlarged cross-sectional view taken along the line 8—8 in FIG. 1.

DETAILED DESCRIPTION OF THE DISCLOSED EMBODIMENT

Figure 2:
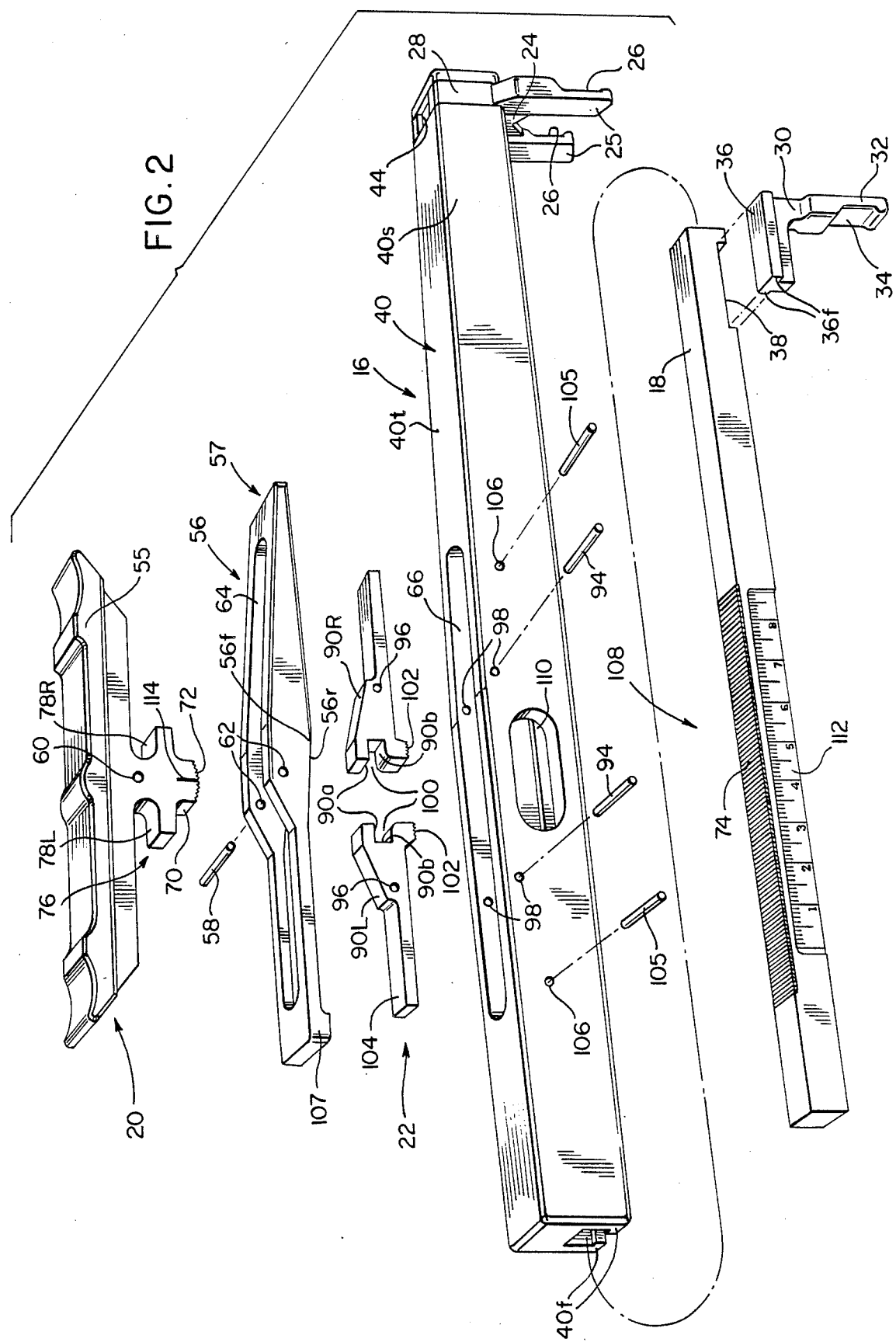
FIG. 2 is an isometric, exploded view of the device shown in FIG. 1.

In general, FIG. 1 illustrates a temporalmandibular joint incrementing device 10 in accordance with the present invention, which is of the type disclosed in U.S. patent application Ser. No. 07/019,459, now U.S. Pat. No. 4,834,112, of which this application is a continuation-in-part, and the disclosure of which, to the extent not inconsistent with this disclosure, is hereby incorporated by reference. Thus, the device 10 comprises first and second retractors (jaws) 12 and 14, which are disposable, with the first retractor being mounted on one end of a fixed support assembly 16 and the second retractor being mounted on a movable actuator rod 18 adjacent the first retractor. An actuator rod operating mechanism 20 is provided adjacent, but in offset relationship to, the center of the support assembly 16, and a releasable actuator rod retaining mechanism 22 is provided on the support assembly adjacent the actuator rod operating mechanism 20.

As is best shown at the right-hand side of FIG. 2 and in FIG. 8, the first retractor 12, which may be of the same general type as disclosed in the above-mentioned application Ser. No. 07/019,459, now U.S. Pat. No. 4,834,112, includes a body 24 provided at a lower end with a pair of spaced patient-engaging legs 25. Each leg 25 has a grooved, flat, tapered seat portion 26 (FIGS. 1 and 2) of substantial size adjacent one end to accommodate the different "bites" of various patients. A pair of spaced resilient clamping legs 28 (best shown in FIG. 2) extend from an opposite upper end of the body 24 in alignment with respective ones of the spaced patient-engaging legs 25 and permit the retractor 12 to be slidably mounted on the support assembly 16 in a linear direction, as illustrated by the arrow in FIG. 2.

The second retractor 14 includes a body portion 30 having a single patient-engaging leg 32 provided with a grooved, flat seat portion 34 (FIGS. 1 and 2), also of substantial size to accommodate the different "bites" of various patients. As is shown in FIGS. 2 and 8, the second retractor 14 also includes a mounting portion 36 receivable in a slot 38 formed in the movable actuator rod 18 and has laterally projecting side flanges 36f, by which the second retractor is retained in the slot.

As is illustrated in FIGS. 2, 7 and 8, the support assembly 16 comprises an inverted, elongated U-shaped channel member or housing 40 having a top wall 40 and spaced depending side walls 40s. The right-hand end of the channel member 40, as viewed in FIG. 2, is provided with an inverted U-shaped slot 44 for receiving the spaced clamping legs 28 of the first retractor 12. Adjacent an upper end, the U-shaped slot 44 is provided with upwardly facing surfaces (not shown) engageable by lug surfaces (not shown) of the legs 28 of the first retractor 12, for retaining the retractor on the channel member 40. At the bottom of the channel member 40, the depending sidewalls 40s include inwardly directed, opposed integral flanges 40f to define a guideway for receiving the actuator rod 18 and the second retractor 14, with the second retractor disposed in the slot 38 (FIGS. 2 and 8) in the actuator rod, for slidable, reciprocable movement.

Referring to FIG. 2, the actuating rod operating mechanism 20 includes an elongated operating handle 55 mounted centrally for pivotable movement in opposite directions on a retaining mechanism releasing or lifting lever 56 of a retractor quick-release mechanism 57, via a pivot pin 58. The operating handle 55, which also forms a part of the retractor quick-release mechanism 57, includes a depending central portion, having an aperture 60, through which the pivot pin 58 extends with its opposite ends disposed in apertures 62 in the retaining mechanism lifting lever 56, and with the depending central portion being disposed in a longitudinally extending slot 64 in the lifting lever and an aligned, longitudinally extending slot 66 in the top wall 40t of the channel member 40. The central depending portion of the operating handle 55 includes an integral drive pawl 70 having teeth 72 engageable with teeth 74 on an upper surface of the actuating rod 18 to drive the actuating rod and the second retractor 14 in opposite directions, depending on the direction in which the operating handle 55 is pivoted. The operating handle 55 also includes a releasing-and-reseating mechanism 76 in the form of a pair of projecting retaining pawl lifting-and-reseating lugs 78L and 78R on opposite sides of the integral drive pawl 70.

Referring further to FIG. 2, the actuating rod retaining mechanism 22 includes a pair of elongated retaining or holding pawl members 90L and 90R mounted for pivotable movement between the sidewalls 40s of the channel member 40 by means of pivot pins 94 extending through apertures 96 in the retaining pawls and aligned apertures 98 in the housing sidewalls. At one end, each of the retaining pawls 90L and 90R includes an open slot 100 for receiving a respective one of the pawl lifting-and-reseating lugs 78L and 78R on the drive pawl 70 in loose-fitting relationship, with an upper wall of each slot 100 defining a pawl lift portion 90a and a lower wall of the slot defining a pawl reseating portion 90b.

Retaining teeth 102, which normally are engaged with the teeth 74 in the upper surface of the actuating rod 18, as shown in FIG. 3, are provided on an underside of the slotted end of each retaining pawl 90. The retaining teeth 102 of each retaining pawl 90 are releasably held in engagement with the actuating rod teeth 74 by an opposite end portion of the retaining pawl, which is in the form of a longitudinally extending resilient leaf spring lever 104 engaged with a pin 105 extending between and having opposite ends disposed in apertures 106 (only one shown) in the sidewalls 40s of the channel member 40.

Thus, as long as the retaining pawl teeth 102 are engaged with the teeth 74 in the actuating rod 18, movement of the actuating rod in either direction is precluded. However, by manually pivoting the operating handle 55 counterclockwise as shown in FIG. 4, or clockwise as shown in FIG. 5, the actuating rod 18, and the retractor 14 thereon, can be moved one precise increment. Further, by manually pivoting the pawl releasing or lifting lever 56 of the retractor quick-release mechanism 57 clockwise, as shown in FIG. 6, the retaining pawls 90L and 90R both are lifted upward to a released position by the lugs 78L and 78R to disengage the pawl teeth 102 from the teeth 74 in the actuating rod 18 so that the actuating rod can be moved manually in either direction, thereby allowing movement of the second retractor 14 to a closed or open position with respect to the first retractor 12 on the channel member 40.

The lifting lever 56 of the retractor quick-release mechanism 57, which straddles the operating handle 55 and on which the operating handle is pivotally mounted by the pin 58, is of relatively rigid, inflexible construction to the right of the pivot pin, as viewed in FIGS. 1-6, and includes arcuate upwardly concave side rocker portions 56r which support the lifting lever on adjacent top surface portions of the channel member 40 for rocking movement. Further, as viewed in FIGS. 1-6, the portion of the lifting lever 56 to the left of the pivot pin 58 is resilient in construction and, at its left-hand end, includes a depending portion 107 which normally rests on an adjacent top surface portion of the channel member 40 when the device 10 is in a locked neutral condition, as shown in FIGS. 1 and 3, being held in this position by the action of the leaf spring lever portions 104 of the retaining pawls 90. At the same time, the rigid right-hand portion of the lifting lever 56 is supported on the adjacent top surface portions of the channel member 40 by the arcuate side rocker portions 56r at an initial fulcrum point 56f located to the right of the pivot pin 58.

The device 10 also may be provided with a scale 108 for the purpose of indicating the number of incremental advances which has occurred at any particular time. The scale 108 includes an elongated slot 110 formed in one of the sidewalls 40s of the channel member 40 and a series of gradations 112 on the actuating rod 18 spaced, for example, 1 mm apart and numbered to represent the number of incremental advances of the actuating rod 18 in response to operation of the operating mechanism 20. Similarly, a reference line or mark 114 is provided on the drive pawl 70 so that as the actuating rod 18 is advanced, the gradations 112 on the actuating rod move with respect to the reference line 114 on the drive pawl to indicate the amount which the actuating rod has moved.

FIGS. 1 and 3 illustrate the device 10 in a neutral condition, and FIG. 4 illustrates a manner of operation of the device to increment the actuating rod 18 to the right in that figure. For this purpose, the user applies downward pressure at the left-hand end of operating handle 55, as indicated by the arrow in FIG. 4, to cause counterclockwise pivotal movement of the operating handle on the retaining pawl lifting lever 56. As will subsequently be described in further detail, this pivoting of the operating handle 55 also causes downward movement of the operating handle-lifting lever pivot pin 58, the operating handle and the integral drive pawl 70.

Initially, the counterclockwise pivoting of the operating handle 55 causes the right-hand lug 78R on the operating handle to produce upward pressure on the lifting portion 90a of the right-hand retaining pawl 90R to lift the teeth 102 of that pawl out of engagement with the teeth 74 on the actuating rod 18. The left-hand teeth 72 on the downwardly moving and pivoting integral drive pawl 70 then engage respective ones of the teeth 74 on the actuating rod 18 to cause the actuating rod to be moved to the right one precise increment (e.g., 1 mm). This incrementing of the actuating rod 18 causes the teeth 102 on the left-hand retaining pawl 90L initially to ride up out of their respective teeth 74 on the actuating rod and then to reseat in the next adjacent teeth in the actuating rod with a tactile and audible feedback "click". The reseating is facilitated by the left-hand lug 78L on the downwardly moving and pivoting operating handle 55 engaging with and exerting downward pressure on the reseating portion 90b of the left-hand pawl 90L.

When the operating handle 55 is pivoted counterclockwise on the retaining pawl lifting lever 56 as shown in FIG. 4, the above-mentioned simultaneous pivoting and downward movement of the operating handle and the integral drive pawl 70 occurs as a result of the arcuate rocker surfaces 56r (FIGS. 1 and 2) formed on the underside of the lifting lever 56, in combination with the resiliency of the left-hand portion thereof. More specifically, as the operating handle 55 is pivoted, the resilient left-hand portion of the lifting lever 56 flexes into a concave downward configuration, and the arcuate rocker surfaces 56r permit the rigid right-hand portion of the lifting lever 56 to rock counterclockwise on the adjacent top surface portion of the channel member 40, with a slight leftward sliding movement (not shown), causing the operating handle-lifting lever pivot pin 58, and thus the operating handle and the integral drive pawl 70, to move downward so that the drive pawl engages the teeth 74 on the actuating rod 18 for an incrementing operation, as above described. When the operating handle 55 is released by the user, the resilient action of the left-hand portion of the lifting lever 56, and of the leaf spring lever portions 104 of the retaining pawls 90, causes the device 10 to return to its initial neutral condition, as shown in FIGS. 1 and 3.

FIG. 5 illustrates a manner of using the incrementing device 10 to cause movement of the actuating rod 18 in an opposite direction, e.g., to the left in FIG. 5. In this regard, the manner of operation is essentially the same as that shown in FIG. 4, except that the user depresses the right-hand end of the operating handle 55, as shown by the arrow in FIG. 5, to cause clockwise pivoting of the operating handle. The left-hand lug 78L on the operating handle 55, through the lifting portion 90a of the left-hand retaining pawl 90L, then initially lifts the teeth 102 of this pawl out of engagement with the respective teeth 74 on the actuating rod 18. At the same time, the downward pressure exerted on the operating handle-lifting lever pivot pin 58 causes flexing of the resilient left-hand portion of the lifting lever 56, and simultaneous rocking of the rigid right-hand portion of the lifting lever counterclockwise, with a slight rightward sliding movement (not shown), thus causing the pivot pin to move downward so that the right-hand teeth 72 on the drive pawl 70 engage respective ones of the teeth 74 on the actuating rod 18, to drive the actuating rod to the left one precise increment.

Simultaneously, as described with reference to the manner of operation in FIG. 4, the teeth 102 on the right-hand retaining pawl 90R ride up out of respective ones of the teeth 74 in the actuating rod 18 and reseat in the next adjacent teeth with a tactile and audible feedback "click", with the reseating being facilitated by the right-hand lug 78R on the operating handle 55 engaging against the reseating portion 90b of the retaining pawl, to urge the pawl downward. Then, when the operating handle 55 is released by the user, the incrementing device 10 again returns to its neutral position, as shown in FIGS. 1 and 3.

FIG. 6 illustrates the manner of using the incrementing device 10 when it is desired to move the actuating rod 18 a significant distance manually as, for example, back to an initial start position after an incrementing operation. This is accomplished by the user exerting downward pressure on the right-hand end of the lifting lever 56 of the retractor quick-release mechanism 57, as indicated by the arrow in FIG. 6, to cause clockwise rocking of the lifting lever on the adjacent top surfaces of the channel member 40, as viewed in this figure. The rocking movement of the lifting lever 56 causes the operating handle-lifting lever pivot pin 58, and thus the operating handle 55, to move vertically upward relative to the channel member 40. As a result, the projecting lugs 78L and 78R on opposite sides of the integral drive pawl 70 of the operating handle 55 exert upward pressure on the lift portions 90a of the retaining pawls 90L and 90R to disengage the teeth 102 on the retaining pawls from the teeth 74 on the actuating rod 18 simultaneously. The actuating rod 18 then may be moved manually in either direction to a desired position, whereupon the lifting lever 56 is released and the incrementing device 10 returns to its neutral position, as shown in FIGS. 1 and 3.

As is shown and described in the above-mentioned U.S. application Ser. No. 07/019,459, now U.S. Pat. No. 4,834,112, in one manner of using the incrementing device 10 in accordance with the invention, in conjunction with a magnetic resonance imaging system, for producing internal images of a temporalmandibular joint of a patient for diagnostic purposes, the patient lies in a prone position on a support table of the magnetic resonance imaging system. Then, with the movable retractor 14 in a zero position, the retractors 12 and 14 are positioned in the patient's mouth with the seats 26 and 34 of the retractors engaging respective ones of the patient's front teeth. The patient then holds the device 10 in one hand so as to be capable of pivoting the operating handle 55, and the imaging procedure is ready to begin. During the imaging procedure, the technician performing the procedure is located in another room at a control panel for the magnetic resonance imaging system.

At the beginning of the imaging procedure, the technician instructs the patient, for example, through a speaker in the magnetic resonance imaging room, to click the device 10 one time. The patient then pivots the operating handle 55 clockwise, as shown in FIG. 5, a full stroke to advance the actuating rod 18 one increment, causing the right-hand retaining pawl 90R to ride out of the teeth 74 in the actuating rod and then to reseat and snap into the next adjacent teeth in the actuating rod with a tactile and loud audible feedback "click". The technician then actuates the magnetic resonance imaging system to produce a series of still images of the temporalmandibular joint of the patient. If necessary, a microphone may be provided in the vicinity of the patient and connected to a speaker in the control room to assist the technician in hearing the clicking of the device 10 as it is actuated by the patient. After completion of the first series of images, the technician advises the patient to operate the device 10 again, whereupon a second series of images is produced. This procedure is continued until the desired incrementing of the temporalmandibular joint and the desired number of images have been generated.

If, during the imaging procedure, the patient experiences pain or discomfort at any specific incrementing step, the patient can signal the technician, who then records the increment advance number of the device 10 at which the pain or discomfort was experienced. Further, at any time in the procedure, the technician can instruct the patient to operate the incrementing device 10 in a reverse direction (to the right in FIG. 4), as for example, to produce another series of images in a previous joint opening position.

Since the device 10 is intended to be used in a magnetic system, the device is formed entirely of non-magnetic material. For example, the device 10 may be formed of a hard, biocompatible plastic, such as polycarbonate, or a plastic sold under the tradename Delrin or Nylon.

While the device 10 has been disclosed in conjunction with producing internal images of a temporalmandibular joint, with the device being operated by the patient, it is contemplated that the device also could be used for other purposes and in other manners. For example, the device 10 could be used in a therapeutic manner, for example, where a physician wants a patient to open the lower jaw to a precise degree each day after undergoing oral surgery, e.g., six clicks for two days, then ten clicks for two days, etc. The principles of the device 10 also could be used for other diagnostic imaging procedures in a magnetic resonance imaging room, such as incremental positioning of a shoulder, knee, etc. It is also contemplated that instead of being manually operated, the device could be remote controlled by air, etc.

In summary, a new and improved device 10 for selectively producing precise incremental movement in a joint of a patient, such as a temporalmandibular joint, in either of two directions, has been disclosed. The device 10 also is operable by the patient in either direction, without the immediate presence of a technician, thus making the device especially suitable in magnetic resonance imaging procedures.

It should be appreciated that the preceding description has been for the purpose of illustration only, and is in no way intended to be limiting. Rather, it is the intention that the present invention be limited only as defined in the appended claims.

What is claimed is:

1. A device for producing precise incremental joint movement in a patient, which comprises:
   first and second spaced retractors for engaging respective body parts of the patient adjacent the joint;
   support means having said first and second retractors mounted thereon for relative movement;
   actuating means mounted on said support means for movement relative to said support means, said actuating means being movable to cause relative movement between said first and second retractors;

operating means movably mounted on said support means for selectively causing a precise preselected incremental movement of said actuating means in either of two opposite directions for a single stroke of said operating means, to cause relative movement between said first and second retractors in the selected direction into successive incremented positions relative to said support means and one another; and means on said support means for retaining said actuating means and said first and second retractors in their relative incremented positions.

2. A device as in claim 1, wherein:
the device is formed entirely of non-magnetic material.

3. A device as in claim 1, which further comprises:
quick-release means for releasing said retaining means so that said actuating means can be moved manually in opposite directions.

4. A device as in claim 1, wherein:
said first and second retractors are disposable.

5. A device as in claim 1, wherein:
said operating means further comprises means for producing a tactile and audible feedback "click" upon each incremental movement of said actuating means.

6. The device as in claim 1, wherein the device is adapted to be operable by one hand of a user and wherein:
said support means comprises a holder portion by which the device is adapted to be held by a user operating the device; and
said operating means is located adjacent said holder portion so that said holder portion and said operating means both can be grasped in one hand of the user and said operating means can be moved by the user on each stroke thereof from an initial position toward said holder portion to cause the precise incremental movement of said actuating means to cause the relative movement between said first and second retractors.

7. The device as in claim 1, wherein:
said support means comprises an elongated, U-shaped channel member; and
said actuating means comprises an elongated rod slidably mounted in said channel member.

8. The device as in claim 7, wherein:
said first retractor is mounted on said U-shaped channel member and includes a pair of spaced patient-engaging legs which define a space therebetween; and
said second retractor is mounted on said elongated rod and includes a single patient-engaging leg which is receivable in the space between the patient-engaging legs on said first retractor when the device is in a start position.

9. The device as in claim 1, wherein:
resilient means is provided for returning said operating means back to its initial position after each operation of said operating means; and
said operating means comprises drive pawl means engageable with teeth on said actuating means to precisely increment said actuating means and said second retractor on each stroke of said operating means, said drive pawl means being movable relative to said teeth as said operating means is moved back to its initial position by said resilient means.

10. The device as in claim 9, which further comprises:
scale means on said actuating means; and
an index mark on said drive pawl means.

11. The device as in claim 9, wherein:
said operating means comprises an operating handle pivotably mounted on said support means for movement in opposite directions.

12. The device as in claim 11, wherein:
said drive pawl means is on said pivoted operating handle and drives said actuating means in the opposite directions.

13. The device as in claim 12, wherein:
said drive pawl means is an integral part of said pivoted operating handle.

14. The device as in claim 9, wherein:
said retaining means comprises first and second releasable pawl means resiliently biased into engagement with the teeth on said actuating means on opposite sides of said drive pawl means.

15. The device as in claim 14, wherein:
said resilient means for returning said operating means back to its initial position, also biases said first and second retaining pawl means into engagement with the teeth on said actuating means.

16. The device as in claim 14, which further comprises:
means on said support means for releasing said first and second retaining pawl means from engagement with the teeth on said actuating means simultaneously, so that said actuating means can be moved manually in the opposite directions.

17. The device as in claim 14, wherein:
said operating means comprises an operating handle mounted on said support means for pivotable movement in opposite directions; and
means are provided on said operating handle for lifting said first retaining pawl means out of engagement with the teeth on said actuating means when the operating handle is pivoted in one direction, and for lifting said second retaining pawl means out of engagement with the teeth on said actuating means when the operating handle is pivoted in the opposite direction.

18. The device as in claim 17, wherein:
said retaining pawl means which is not lifted by said lifting means on said operating handle rides out of respective teeth on said actuating means in response to movement of said actuating means by said drive pawl means and reseats in adjacent teeth on said actuating means; and
means are provided on said operating handle for facilitating the reseating of said unlifted retaining pawl means in the adjacent teeth on said actuating means.

19. The device as in claim 14, wherein:
said operating means comprises an operating handle mounted on said support means for pivotable movement in opposite directions; and
said operating handle includes means for releasing said first and second retaining pawl means from engagement with the teeth on said actuating means simultaneously, so that said actuating means can be moved manually in opposite directions.

20. The device as in claim 19, wherein:
said means on said operating handle for releasing said first and second retaining pawl means simultaneously includes lifting lugs engageable with lift portions on respective ones of said retaining pawl means.

21. The device as in claim 20, which further comprises:
 means mounted on said support means for lifting said operating handle relative to said support means, to release said first and second retaining pawl means simultaneously.

22. The device as in claim 21, wherein:
 said operating handle lifting means is a lifting lever mounted on said support means.

23. The device as in claim 22, wherein:
 said operating handle is pivoted on said lifting lever.

24. The device as in claim 23, wherein:
 said operating handle is pivoted on said lifting lever intermediate opposite ends of said lifting lever.

25. The device as in claim 24, wherein:
 said lifting lever is mounted for rocking movement on said support means, with one end portion of said lifting lever being of rigid construction and an opposite end portion of said lifting lever being of resilient construction.

26. The device as in claim 14, wherein each of said retaining pawl means comprises:
 an elongated retaining pawl member having first and second opposite ends and pivoted intermediate said opposite ends on said support means;
 retaining teeth adjacent said first end of said pawl member and engageable with the teeth on said actuating means; and
 a resilient lever portion adjacent said second end of said pawl member and biased against said support means to urge the retaining teeth on said pawl member into engagement with the teeth on said actuating means.

27. The device as in claim 26, wherein:
 said operating means comprises an operating handle mounted on said support means for pivotable movement in opposite directions;
 each of said retaining pawl members includes a pawl member lift portion; and
 said operating handle has lugs projecting from opposite sides of said drive pawl means, at least one of said lugs being engageable with a respective one of said lift portions on the associated pawl member as said operating handle is moved relative to said support means, to lift said retaining pawl member from the teeth on said actuating means.

28. The device as in claim 27, wherein:
 said lift portion of each retaining pawl member is defined by a slot which also defines a retaining pawl member reseating portion; and
 each lug on said operating handle projects into the slot in the respective retaining pawl member.

29. The device as in claim 28, which further comprises:
 lever means mounted on said support means for lifting said operating handle relative to said support means, to release said first and second retaining pawl members simultaneously, said operating handle being pivoted on an intermediate portion of said lifting lever means.

30. A device as in claim 1, which further comprises:
 an operating handle forming part of said operating means and having an integral drive pawl engageable with teeth on said actuating means, said operating handle being pivotable in opposite directions to cause said drive pawl to precisely increment said actuating means and said second retractor on each stroke of said operating handle;
 first and second retaining pawl members forming parts of said retaining means and pivotably mounted on said support means on respective opposite sides of said drive pawl;
 first and second resilient means for biasing said first and second retaining pawl members, respectively, into engagement with the teeth on said actuating means, said first and second resilient means also returning said operating handle to a neutral position after each operation of said operating handle;
 means on said operating handle for lifting said retaining pawl members from engagement with the teeth on said actuating means, said lifting means lifting one of said retaining pawl members when the operating handle is pivoted on one direction, and lifting the other of said retaining pawl members when the operating handle is pivoted in the opposite direction, with said unlifted retaining pawl member riding out of the respective teeth on said actuating means in each instance as said actuating means is incremented by said drive pawl;
 reseating means on said operating handle for reseating each unlifted retaining pawl member into the next adjacent teeth in said actuating means with a tactile and audible feedback "click" as said operating handle is pivoted in an incrementing operation; and
 a retractor quick-release mechanism comprising lever means mounted on said support means for lifting said operating handle relative to said support means, to lift both of said retaining pawl members out of engagement with the teeth on said actuating means simultaneously, so that said actuating means can be moved manually in opposite directions, said operating handle being pivoted on said lifting lever means.

* * * * *